United States Patent [19]

Howard et al.

[11] Patent Number: 5,049,394

[45] Date of Patent: Sep. 17, 1991

[54] PHARMACEUTICAL COMPOSITION CONTAINING HIGH DRUG LOAD AND METHOD FOR PREPARING SAME

[75] Inventors: John R. Howard; Anne M. Delargy, both of Merseyside, United Kingdom

[73] Assignee: E. R. Squibb & Sons, Inc., Princeton, N.J.

[21] Appl. No.: 323,717

[22] Filed: Mar. 15, 1989

Related U.S. Application Data

[63] Continuation of Ser. No. 95,498, Sep. 11, 1987, abandoned.

[51] Int. Cl.$^5$ .............................. A61K 9/16; A61K 9/50
[52] U.S. Cl. ..................................... 424/490; 424/452; 424/458; 424/489; 424/493; 424/494
[58] Field of Search .......................... 424/489, 490, 494

[56] References Cited

U.S. PATENT DOCUMENTS 4,711,777  12/1987  Tan et al. ............................... 424/79
4,808,413   2/1989  Joshi et al. ........................... 424/458

FOREIGN PATENT DOCUMENTS 2098867A  12/1982  United Kingdom .

Primary Examiner—Thurman K. Page
Assistant Examiner—James Spear
Attorney, Agent, or Firm—Burton Rodney

[57] ABSTRACT

A pharmaceutical composition in the form of beads prepared by an extrusion-spheronization technique and containing more than 80% by weight drug, less than 15% by weight non-lipophilic binder-plasticizer, such as microcrystalline cellulose to achieve required plasticity for processing, a starch-based excipient such as sodium starch glycolate or pregelatinized starch to control water/fluid distribution and thereby inhibit agglomeration during processing, and water-soluble binder such as hydrolyzed gelatin to make the final beads less friable. During processing a granulating agent such as ethanol/water is added to improve blend properties and control during spheronization. A method for preparing the above beads is also provided.

19 Claims, No Drawings

PHARMACEUTICAL COMPOSITION CONTAINING HIGH DRUG LOAD AND METHOD FOR PREPARING SAME

REFERENCE TO OTHER APPLICATIONS

This application is a continuation of application Ser. No. 95,498 filed Sept. 11, 1987 now abandoned.

FIELD OF THE INVENTION

The present invention relates to a pharmaceutical composition in the form of beads or spheroids, which contain more than 80% by weight drug and are prepared by an improved extrusion/spheronization process.

BACKGROUND OF THE INVENTION

Extrusion/spheronization is a relatively complex technique used for the preparation of pharmaceuticals in the form of beads or spheroids (0.5–1.5 mm in diameter). The process of manufacture involves dry blending drug and excipients, wet granulation (aqueous or non-aqueous) of the mass, extrusion through a screen of defined pore size and spheronization. During the extrusion process, the wet mass is formed and compacted into cylindrical strands. To obtain spheres, the cylindrical strands are placed in a spheronizer, which is simply a unit containing a rotating disc. The cylindrical strands break up under the action of the rotating disc, and the short strands deform to form spheres, by a tumbling-/roping action.

To undergo this process, it is recognized that the blend of drug and excipients should exhibit a high degree of plasticity to allow the extrusion and spheronization (deformation) process to occur. To achieve the required plasticity Avicel (microcrystalline cellulose, of various grades, PH 101, PH 102, PH 103, PH 105, RC 591, RC 581 CL-611) is added to the blend. In addition, the fluid used in wet massing adds plasticity to the blend; the wetter the mass the more plastic the blend becomes. However, fluid levels need to be carefully controlled, as agglomeration (balling up) will occur during spheronization of an over wet extrudate.

It has been found that for a blend of drug and excipients to achieve an acceptable degree of plasticity to allow the extrusion and spheronization process to occur, the blend should not contain more than 75–80% by weight of the drug component and should not contain less than 15–20% of a microcrystalline cellulose component. Gamlen, M. J., Manuf. Chem., June, 1985, p. 55 and O'Connor, R. E. and Schwartz, J. B., Drug Dev. Ind. Pharm. II, 1837, 1985.

Although the above-described prior art extrusion/spheronization technique is satisfactory to produce beads containing drug loads of up to 75 to 80%, still, there is a need for beads containing more than 80% drug. Thus, for example, it has been found that erythromycin beads containing 70 to 75% erythromycin and 15 to 20% microcrystalline cellulose may not have the desired drug dissolution rate due to the presence of the large amounts of microcrystalline cellulose; in addition, the drug dose would not fit comfortably into a size 0 capsule.

DESCRIPTION OF THE INVENTION

In accordance with the present invention, a novel pharmaceutical composition is provided which may contain 80% or more drug component, will have the desired dissolution rate and which may be readily prepared using extrusion/spheronization techniques. This is indeed surprising and unexpected inasmuch as until now, it has been thought that beads containing 80% or more drug could not be readily produced due to plasticity problems during extrusion and/or agglomeration problems during spheronization.

The pharmaceutical composition in accordance with the present invention will be in the form of beads containing more than about 80% by weight drug, less than about 15% by weight and preferably less than about 10% by weight, non-lipophilic binder-plasticizer, such as microcrystalline cellulose, to achieve desired drug dissolution rate, a starch-based excipient, such as sodium starch glycolate or pregelatinized starch to bind and plasticize the blend and to control water/fluid distribution and thereby inhibit agglomeration during processing, and optionally a water-soluble binder, such as hydrolyzed gelatin, to reduce friability in final beads. As will be seen hereinafter, during processing, a granulating agent, such as ethanol/water mixture, is added to improve blend properties.

In addition, in accordance with the present invention, a process is provided for preparing the above-described pharmaceutical composition in the form of beads, which process includes the steps of mixing the medicament or drug with binder-plasticizer in amounts of less than about 15% by weight of the final product and with starch-based excipient and optionally water-soluble binder and a granulating agent (aqueous and/or non-aqueous such as water/ethanol) to form a wet mass, extruding the wet mass to form an extrudate and spheronizing the extrudate to form beads. The beads may then be dried and optionally coated as described herein.

It has been surprisingly found that with the presence of binder-plasticizer, such as microcrystalline cellulose, in amounts less than about 15% and preferably less than about 10% by weight, the plasticity of the wet mass is reduced but a desirable bead dissolution rate is achieved; with the presence of starch-based excipient such as sodium starch glycolate, blend properties including plasticity are enhanced to ensure effective extrusion and spheronization without agglomeration; with the presence of water-soluble binder such as hydrolyzed gelatin, the level of fluid is controlled so as to avoid agglomeration during spheronization, and with the presence of the aqueous/non-aqueous granulating agent, further control of the spheronization process is achieved. Thus, the above-described blend assumes properties which allows both extrusion and controlled spheronization of product. The above is achieved even with the presence of high drug loads of at least 80% by weight or more while employing exceedingly small amounts of binder-plasticizer such as microcrystalline cellulose.

The beads of the invention will contain from about 80 to about 96% by weight medicament and preferably from about 80 to about 94% by weight medicament. Medicaments which may be used herein include angiotensin converting enzyme inhibitors including substituted proline derivatives, such as any of those disclosed in U.S. Pat. No. 4,105,776 to Ondetti et al mentioned above, with captopril, that is, 1-[(2S)-3-mercapto-2-methylpropionyl]-L-proline, being preferred, ether and thioether mercaptoacyl prolines such as any of those disclosed in U.S. Pat. No. 4,316,906 to Ondetti et al with zofenopril being preferred, carboxyalkyl dipeptide derivatives, such as any of those disclosed in U.S. Pat. No. 4,374,829 mentioned above, with N-(1-ethoxycarbonyl-3-phenylpropyl)-L-alanyl-Lproline, that is (enalapril).

Other examples of angiotensin converting enzyme inhibitors suitable for use herein include any of the phosphinylalkanoyl prolines disclosed or covered in U.S. Pat. No. 4,168,267 mentioned above, any of the phosphinylalkanoyl substituted prolines including fosinopril disclosed or covered in U.S. Pat. No. 4,337,201 discussed above, any of the 1-(3-mercapto-2-methylpropanoyl)prolyl amino acid derivatives disclosed or covered in U.S. Pat. No. 4,248,883, the phosphonamidates disclosed or covered in U.S. Pat. No. 4,432,971 and any of the phosphonates disclosed or covered in U.S. Pat. No. 4,452,790 such as (S)-1-[6-amino-2-[[hydroxy(4-phenylbutyl)phosphinyl]oxy]-1-oxohexyl]-L-proline discussed above.

The disclosure of all of the above-mentioned U.S. patents are incorporated herein by reference.

The beads of the invention may contain other medicaments which are absorbed in the upper intestines, including anti-hypertensive agents such as nifedipine and verapamil, diuretics such as hydrochlorothiazide, bendroflumethiazide or chlorthalidone, beta-blockers such as proprano-lol HCl or atenolol and anti-infectives such as erythromycin, beta lactams, penicillins, other macrolides or lincosamides.

The non-lipophilic binder-plasticizer will be present in an amount within the range of from about 1 to about 12% or more (but less than 15%) by weight of the bead and preferably from about 2 to about 8% by weight of the bead. Preferred binder-plasticizer for use in the bead of the invention will be microcrystalline cellulose. In such case the binder may serve as an excipient as well. However, other binders may be employed by themselves or together with known excipeints. Such binders may be hydrophilic polymers or hydrocolloids formed of water-swellable polymeric substances such as cellulosic polymers and gums.

The starch-based excipient is present to improve overall blend properties including quality of the wet mass to be extruded and the resultant extrudate and allow for controlled spheronization. It is theorized that the starch-based excipient affects the availability of moisture in the blend. During extrusion, sufficient water (or other fluid) is available to plasticize and lubricate the blend. However, during the spheronization, the starch-based excipient appears to prevent or retard water/fluid build up at the surface of the bead, thereby inhibiting agglomeration.

The starch-based excipient will be present in an amount within the range of from about 0.5 to about 12% by weight of the bead and preferably from about 1 to about 10% by weight of the bead. Preferred starch-based excipient for use in the bead of the invention will be sodium starch glycolate. Other starch-based excipients suitable for use herein include, but are not limited to, corn starch, pregelatinized starch (starch 1500), croscarmellose or cross-linked polyvinylpyrrolidone.

The water-soluble binder is optionally present to reduce level of fluid in the mass to be extruded, to improve plasticity and to ensure that agglomeration will not occur during spheronization and to produce beads which are less friable than beads heretofore prepared. Thus, in preferred embodiments, the water-soluble binder will be present in an amount within the range of from about 0.2 to about 5% and preferably from about 0.5 to about 3% by weight of the bead. Examples of water-soluble binders suitable for use herein include, but are not limited to hydrolyzed gelatin, polyvinylpyrrolidone or low viscosity hydroxypropylmethyl cellulose, with hydrolyzed gelatin being preferred.

The optional water-soluble binder will be dissolved in a granulating fluid which preferably is water or an ethanol/water solution containing from 0 to about 75% by weight ethanol and preferably from 0 to about 30% by weight ethanol. Other granulating fluids may be employed including isopropyl alcohol, methanol or other suitable organic solvent.

A preferred bead in accordance with the present invention will include a core containing from about 80 to about 95% by weight medicament, from about 2 to about 5% by weight of microcrystalline cellulose, from about 2% to about 5% by weight starch-based excipient, such as sodium starch glycolate or pre-gelatinized starch, and optionally from about 0.5 to about 3.5% by weight of water soluble binder which preferably is hydrolyzed gelatin (all of such % being based on the weight of the core).

Optional inert fillers which may be present include lactose, sucrose, mannitol, xylitol and the like.

In forming the beadlets in accordance with the process of the invention, the medicament and defined excipients are thoroughly mixed with granulating agent such as water or ethanol/water (up to 3:1) optionally containing water-soluble binder such as hydrolyzed gelatin, for example, using a conventional blender to form a wet mass. Thereafter, the wet mass is extruded, for example, employing a Nica, Luwa or other type extruder to form an extrudate which is then passed through spheronizing equipment, such as Nica, Luwa or other type, which converts the extrudate into beads of appropriate particle size range. The beads may then be dried by tray drying oven or fluid bed drying. If desired, the beads may be coated, for example, with a solution or dispersion of film former and plasticizer by pan coating, fluid bed coating and the like.

The so-formed beads may be filled into hard shell capsules to provide formulations administered in single or divided doses of from about 5 to 300 mg, preferably from about 6.25 to about 250 mg/one to four times daily.

The following Examples represent preferred embodiments of the present invention. Unless otherwise indicated, all temperatures are expressed in degrees Centigrade.

EXAMPLE 1

A bead formulation containing 92.5% erythromycin and having the following composition was prepared as described below.

| Ingredient | Amount in % Weight |
| --- | --- |
| Erythromycin | 92.5 |
| Sodium starch glycolate (Primojel) | 3 |
| Microcrystalline cellulose* (Avicel pH 101-binder/plasticizer) | 3.5 |
| *Hydrolyzed gelatin (binder added in granulating fluid as 5% w/v solution) | 1 |

The above ingredients were mixed and kneaded using water/25% ethanol as a granulating fluid in a planetary mixer to form a wet mass. The wet mass was passed through a Nica E140 extruder to form an extrudate (~1 mm diameter). The extrudate was then passed through a Nica spheronizer to form beads. The beads were then dried at 50° C. in a tray drying oven or in a fluid bed dryer. A fraction of the so-formed beads were filled into hard shell pharmaceutical capsules to form a formulation of the invention.

EXAMPLE 2

An erythromycin bead formulation having the following composition was prepared as described in Example 1.

| Ingredient | % by Weight |
|---|---|
| Erythromycin Base USP | 87.5 |
| Sodium starch glycolate | 2 |
| Pregelatinized starch | 7 |
| Microcrystalline cellulose | 3.5 |

The core was manufactured as described in Example 1 except water was employed as the granulating fluid.

What is claimed:

1. A method for preparing a pharmaceutical composition in the form of a bead having a diameter of 0.5 to 1.5 mm and containing more than about 80% by weight medicament, which comprises forming a wet mass of medicament, non-lipophilic binder-plasticizer which is a microcrystalline cellulose in an amount within the range of from about 1 to about 15% by weight of the final composition, starch-based excipient in an amount within the range of from about 0.5 to about 12% by weight of the final composition, wherein the starch-based excipient is sodium starch glycolate, corn starch, croscarmellose, pregelatinized starch or mixtures thereof, and optionally water-soluble binder with a granulating fluid, extruding said wet mass to form an extrudate and forming said extrudate into beads and drying said beads.

2. A pharmaceutical composition in the form of a bead containing a high medicament load, comprising a medicament in an amount of more than about 80% by weight of the composition, a non-lipophilic binder-plasticizer which is microcrystalline cellulose in an amount within the range of from 1 to about 15% by weight of said composition, a starch-based excipient in an amount within the range of from about 0.5 to about 12% by weight of said composition, wherein the starch-based excipient is sodium starch glycolate, corn starch, croscarmellose, pregelatinized starch or mixtures thereof, and optionally a water-soluble binder, prepared by the process as defined in claim 1.

3. The composition as defined in claim 2 wherein said non-lipophilic binder-plasticizer is present in an amount within the range of from about 2 to about 12% by weight of the composition.

4. The composition as defined in claim 2 wherein the starch-based excipient is present in an amount within the range of from about 1 to about 10% by weight of the composition.

5. The composition as defined in claim 2 wherein the water-soluble binder is present in an amount within the range of from about 0.2 to about 5% by weight of the composition.

6. The composition as defined in claim 2 wherein the starch-based excipient is sodium starch glycolate, croscarmellose, pregelatinized starch, or mixtures thereof.

7. The composition as defined in claim 2 wherein said medicament is an angiotensin-converting enzyme (ACE) inhibitor.

8. The composition as defined in claim 7 wherein said ACE inhibitor is selected from the group consisting of a substituted proline derivative, an ether or thioether mercaptoacyl proline, a carboxyalkyl dipeptide derivative, a phosphinylalkanoyl proline derivative, a phosphonamidate derivative, a phosphonate derivative and a prolylamino acid derivative.

9. The composition as defined in claim 7 wherein said ACE inhibitor is captopril.

10. The composition as defined in claim 8 wherein said ACE inhibitor is zofenopril or fosinopril.

11. The composition as defined in claim 8 wherein said ACE inhibitor is enalapril.

12. The composition as defined in claim 2 wherein the medicament is erythromycin.

13. The composition as defined in claim 2 wherein said medicament is captopril or erythromycin, said binder-plasticizer is microcrystalline cellulose, said starch-based excipient is sodium starch glycolate or pregelatinized starch and said water-soluble binder is hydrolyzed gelatin.

14. The composition as defined in claim 2 including a film-coating on said beads.

15. The composition as defined in claim 2 wherein said medicament is present in an amount within the range of from about 80 to about 95% by weight of said composition.

16. The method as defined in claim 1 wherein said medicament is an ACE inhibitor.

17. The method as defined in claim 1 wherein said binder-plasticizer is microcrystalline cellulose, and starch-based excipient is sodium starch glycolate, and said water-soluble binder is hydrolyzed gelatin.

18. The method as defined in claim 1 wherein said granulating fluid is an ethanol/water solution.

19. The method as defined in claim 1 further including the step of applying a film coating on the dried beads.

* * * * *